(12) United States Patent
Hong

(10) Patent No.: US 9,101,466 B2
(45) Date of Patent: Aug. 11, 2015

(54) INTRAOCULAR LENS WITH EXTENDED DEPTH OF FOCUS

(71) Applicant: Novartis AG, Basel (CH)

(72) Inventor: Xin Hong, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/454,251

(22) Filed: Aug. 7, 2014

(65) Prior Publication Data

US 2014/0350672 A1    Nov. 27, 2014

Related U.S. Application Data

(62) Division of application No. 12/634,026, filed on Dec. 9, 2009, now abandoned.

(60) Provisional application No. 61/138,816, filed on Dec. 18, 2008.

(51) Int. Cl.
*A61F 2/16* (2006.01)
*G02C 7/04* (2006.01)

(52) U.S. Cl.
CPC . *A61F 2/16* (2013.01); *A61F 2/164* (2015.04); *A61F 2/1613* (2013.01); *A61F 2/1618* (2013.01); *A61F 2/1624* (2013.01); *A61F 2/1637* (2013.01); *G02C 7/04* (2013.01); *G02C 7/041* (2013.01); *G02C 2202/20* (2013.01)

(58) Field of Classification Search
None
See application file for complete search history.

(56) References Cited

U.S. PATENT DOCUMENTS

| | | | |
|---|---|---|---|
| 4,995,715 A * | 2/1991 | Cohen | 351/159.44 |
| 5,699,142 A | 12/1997 | Lee et al. | |
| 5,922,821 A | 7/1999 | Lebouef et al. | |
| 6,338,559 B1 | 1/2002 | Williams et al. | |
| 6,353,069 B1 | 3/2002 | Freeman et al. | |
| 6,533,416 B1 * | 3/2003 | Fermigier et al. | 351/159.22 |
| 6,786,928 B2 | 9/2004 | Callahan et al. | |
| 6,884,263 B2 | 4/2005 | Valyunin et al. | |
| 6,923,539 B2 | 8/2005 | Simpson et al. | |
| 2004/0207807 A1 * | 10/2004 | Lindacher | 351/160 R |
| 2004/0230299 A1 * | 11/2004 | Simpson et al. | 623/6.11 |
| 2007/0258143 A1 | 11/2007 | Portney | |

FOREIGN PATENT DOCUMENTS

| | | |
|---|---|---|
| EP | 0605841 | 7/1994 |
| WO | WO 2006/023404 | 3/2006 |

OTHER PUBLICATIONS

European Search Report for Application No. 09833807.2, Publication No. EP 2358306, Published Aug. 24, 2011, dated Apr. 24, 2012, 2 pages.

(Continued)

*Primary Examiner* — Andrew Iwamaye
*Assistant Examiner* — Leslie Lopez
(74) *Attorney, Agent, or Firm* — Haynes and Boone, LLP

(57) ABSTRACT

An ophthalmic lens is disclosed, one embodiment comprising an optic having an anterior surface and a posterior surface disposed about an optical axis, wherein at least one of the surfaces has a profile characterized by superposition of a base profile and an auxiliary profile, the auxiliary profile comprising a continuous pattern of surface deviations from the base profile. The auxiliary profile is a sinusoidal profile and can be amplitude modulated, frequency modulated or both amplitude and frequency modulated. The ophthalmic lens can be an IOL.

24 Claims, 13 Drawing Sheets

(56) References Cited

OTHER PUBLICATIONS

PCT International Preliminary Report on Patentability and Written Opinion of the International Searching Authority, International Application No. PCT/US2009/067287, dated Jun. 21, 2011, 5 pages.

International Search Report for PCT/US2009/067287, Publication No. WO2010/071751, dated Feb. 5, 2010, 2 pages.

* cited by examiner

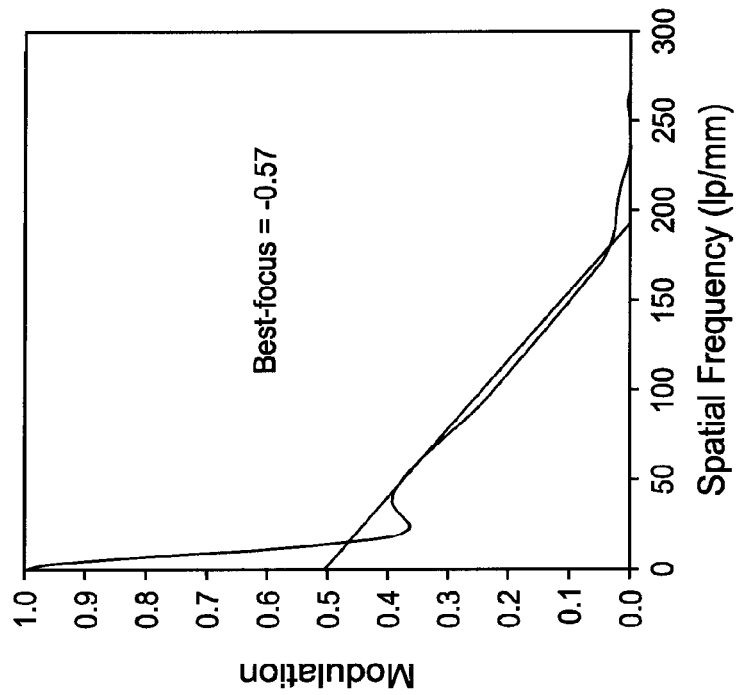
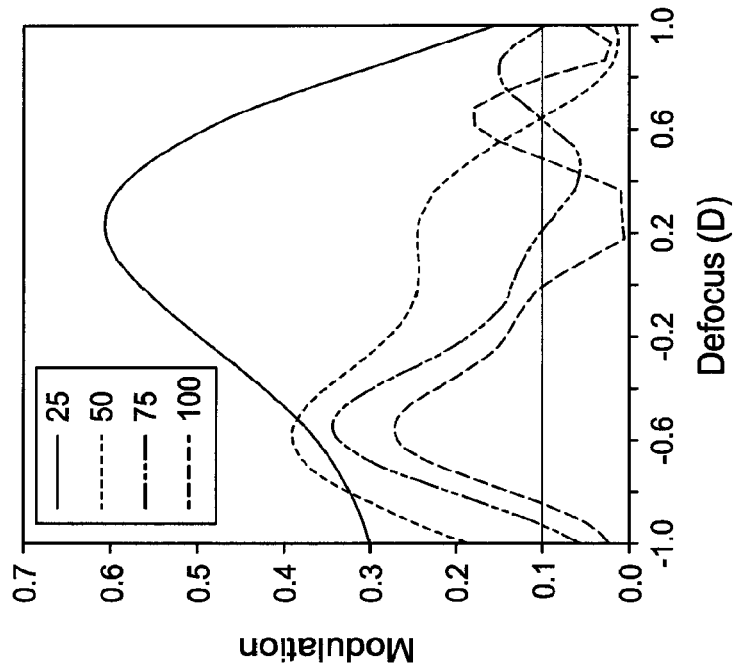

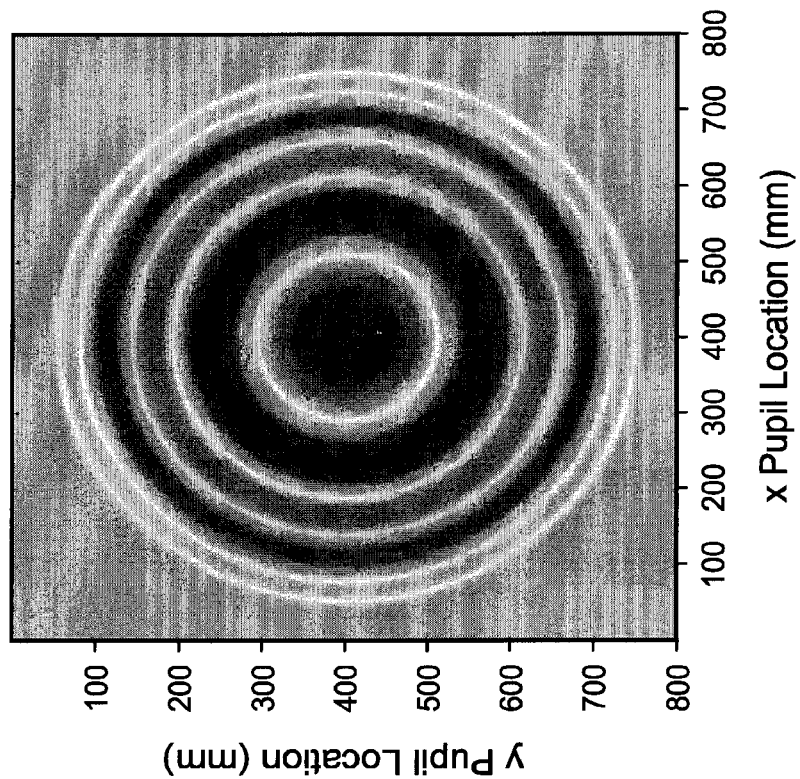
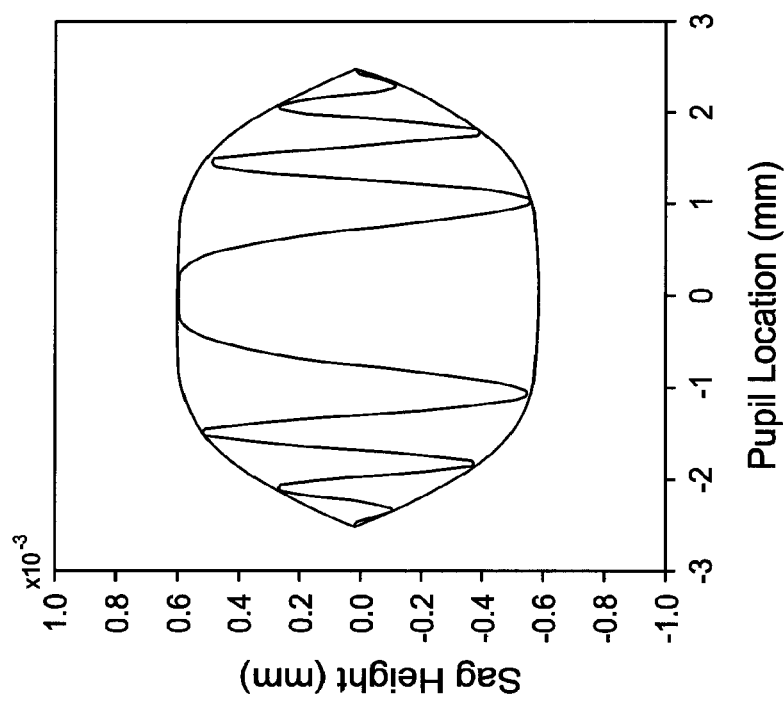
Fig. 4B
Fig. 4A

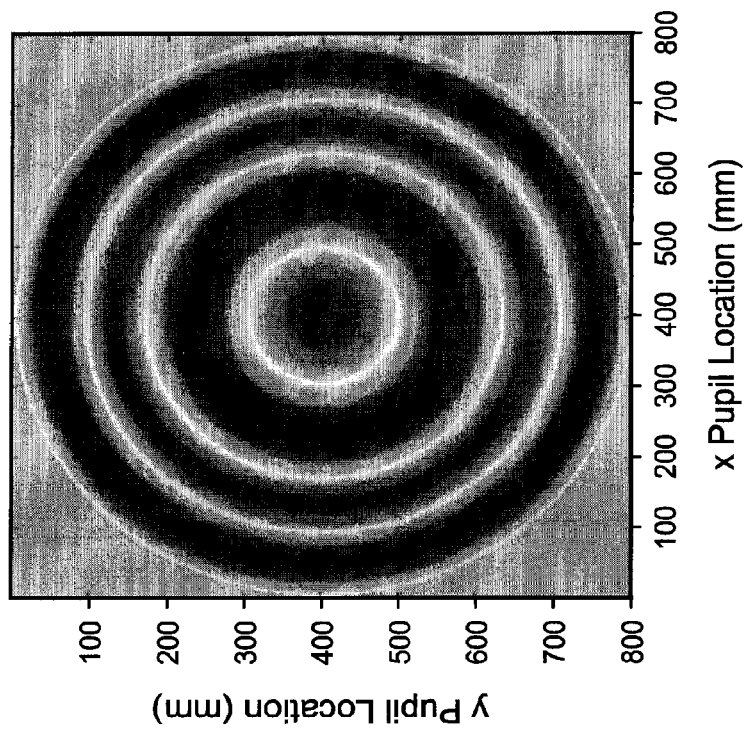
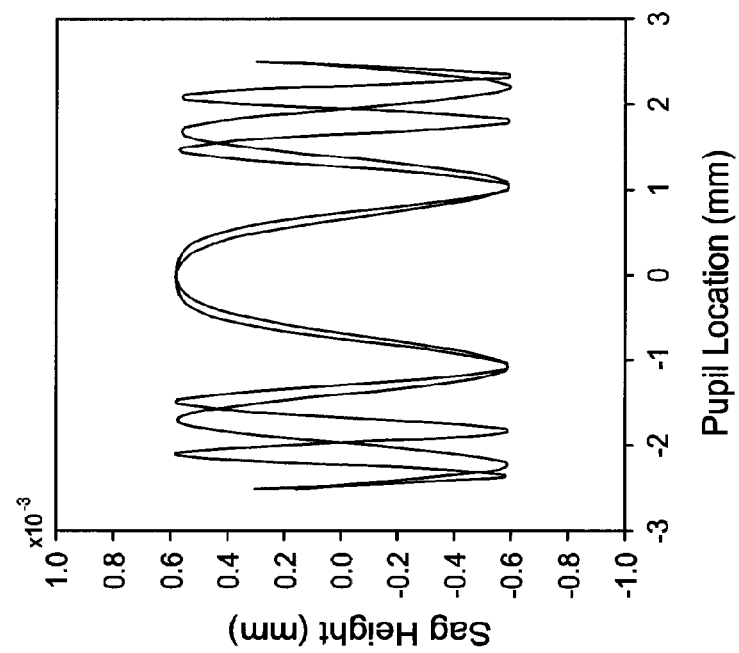
Fig. 5B
Fig. 5A

INTRAOCULAR LENS WITH EXTENDED DEPTH OF FOCUS

CROSS-REFERENCE TO RELATED APPLICATIONS

This application is a divisional of U.S. patent application Ser. No. 12/634,026, filed Dec. 9, 2009, which claims priority to U.S. Provisional Application Ser. No. 61/138,816 filed Dec. 18, 2008, both of which are incorporated herein by reference in their entireties.

FIELD OF THE INVENTION

The present invention relates generally to ophthalmic lenses, and more particularly to ophthalmic lenses that provide an enhanced depth of focus.

BACKGROUND OF THE INVENTION

Intraocular lenses are routinely implanted in patients' eyes during cataract surgery to replace the natural crystalline lens. A variety of ophthalmic lenses are employed for correcting visual disorders, such as, cataract, myopia, hyperopia or astigmatism. For example, an intraocular lens (IOL) can be implanted in a patient's eye during cataract surgery to compensate for the lost optical power of the removed lens. In many cases, however, the implanted lens may not provide the best focus at the targeted object distance.

The design of modern conventional IOL optics is mainly focused on two outcomes: an optic that provides aberration correction to provide clear distance vision, or a multifocal optic that can provide far vision while also providing for near vision needs. These designs do not typically address another important patient need, namely: for most elderly patients, the majority of visual needs are focused around certain intermediate distances. These elderly patients, who form a large percentage of patients receiving IOLs to replace a natural lens, require an extended functional vision, from distance to intermediate, to perform daily chores. This extended functional vision is not sufficiently provided for by current IOL designs.

Accordingly, there is a need for an improved ophthalmic lens, and, more particularly, for an improved IOL, that can provide an enhanced depth of focus compared to prior art IOLs.

SUMMARY OF THE INVENTION

The present invention provides ophthalmic lenses that exhibit extended depth of field while providing sufficient contrast for resolution of an image over a selected range of defocus distances. Embodiments of the present invention incorporate sinusoidal optic designs in an IOL to provide an extended depth-of-focus in a human eye. Based on a classical sinusoidal technique, embodiments of the present invention incorporate amplitude modulation and frequency modulation techniques to provide enhanced depth of focus. One embodiment can provide for attenuation of the sinusoidal amplitude from pupil center to lens periphery, concentrating more light energy to a single focal plane. Another embodiment can provide for modulating the sinusoidal periodicity of the IOL optic to change the effective lens add-power as a function of pupil radius. An embodiment combining amplitude modulation and frequency modulation on a sinusoidal curve can further enhance the IOL through-focus performance and generate a desirable depth-of-focus profile free of certain photic phenomena experienced with conventional designs. Embodiments of the optic design of the present invention can be applied to single focus, multifocal and/or accommodative IOL optics.

Methods of correcting refractive errors or otherwise enhancing vision over a range of distances are disclosed, as well as methods of manufacturing the lenses of the present invention. The ophthalmic lenses of the present invention can be used in various vision correction applications including, but not limited to, IOLs that can be used for both pseudophakic and phakic applications. The invention can also be useful in connection with contact lenses, intrastromal implants and other refractive devices.

The terms "depth of field" and "depth of focus" in the context of a lens/IOL are well known and readily understood by those skilled in the art as referring to the distances in the object and image spaces over which an acceptable image can be resolved. To the extent that a quantitative measurement is necessary to describe the present invention, the term "depth of field" or "depth of focus" as used herein, more specifically can be measured by an amount of defocus associated with the lens at which a through-focus modulation transfer function (MTF) of the lens measured with a 3 mm aperture and green light, e.g., light having a wavelength of about 550 nm, exhibits a contrast of at least about 15% at a spatial frequency equal to about one-third of the diffraction limited spatial frequency associated with that lens. Other definitions can also be applied and it should be clear that depth of field is influenced by many factors including, for example, aperture size, chromatic content of the light from the image, and base power of the lens itself.

An IOL according to the teachings of the invention can have any nominal power suited for a particular application. In one embodiment, particularly suited for IOL applications for cataract patients, an ophthalmic lens of the invention can exhibit a nominal power in a range of about 17 to about 25 Diopters. In other applications, phakic lenses having negative nominal power can be formed according to the teachings of the invention.

The lens body of a lens according to the teachings of the invention can be formed of any suitable biocompatible material. For example, the lens body can be formed of a soft acrylic, such as the AcrySoft material manufactured by Alcon Laboratories, Inc., of Fort Worth, Tex., hydrogel, or silicone material. For example, the lens body can be formed of polymethyl methacrylate (PMMA). In some embodiments, especially when a foldable IOL lens is desired, the lens can be formed of a copolymer of acrylate and methacrylate. For illustrative examples of such copolymer compositions, see for example, U.S. Pat. No. 5,922,821 entitled "Ophthalmic Lens Polymers" issued to Lebouef et al. on Jul. 13, 1999 and U.S. Pat. No. 6,353,069 entitled "High Refractive Index Ophthalmic Device Materials" issued to Freeman et al. on Mar. 5, 2002, the teachings of both of which are hereby incorporated by reference.

Further understanding of the invention can be obtained by reference to the following detailed description and the associated drawings, which are described briefly below.

BRIEF DESCRIPTION OF THE DRAWINGS

FIGS. 2A-2D illustrate the through-focus performance of a sinusoidal lens design for different pupil sizes;

FIGS. 4A and 4B show surface profile plots of an amplitude-modulated sinusoidal optic design;

FIGS. 5A and 5B show surface profile plots of a frequency-modulated sinusoidal optic design;

DETAILED DESCRIPTION OF THE INVENTION

The present invention provides an ophthalmic lens that exhibits an extended depth of field by combining amplitude modulation and frequency modulation on a sinusoidal curve. A lens of the invention can thus correct refractive errors or otherwise enhance vision by providing sufficient contrast for resolution of an image over a selected range of defocus distances that are commensurate with an enhanced depth of field exhibited by the lens.

Figure 1:
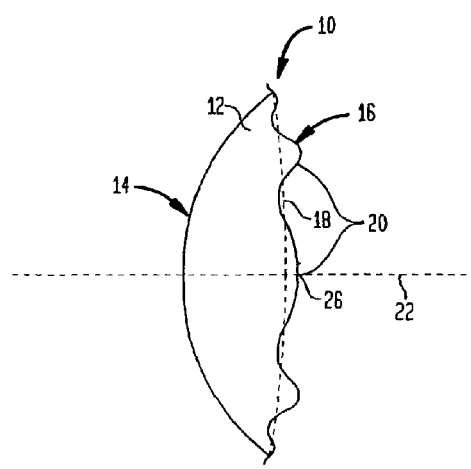
FIG. 1 schematically depicts a lens according to the teachings of this invention.
Figure 1:
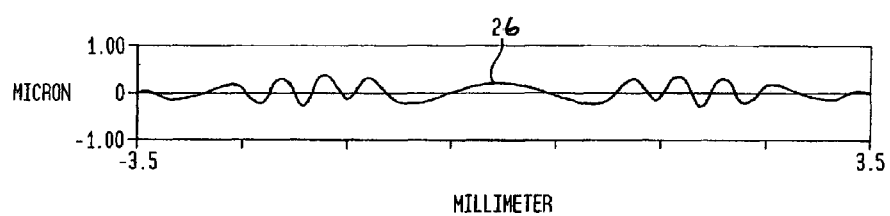

FIG. 1 illustrates schematically an exemplary lens 10 according to the teachings of this invention that includes a lens optic 12 having two refractive surfaces 14 and 16. Although the refractive surfaces are depicted as being generally convex, either surface can have a generally concave shape. Alternatively, the surfaces 14 and 16 can be selected to generate a plano-concave or a plano-convex lens. Hence, a lens according to the teachings of the invention can have positive or negative nominal power.

The lens optic 12 can be formed from a variety of biocompatible soft materials. For example, the lens optic 12 can be formed of a soft acrylic material, e.g., a copolymer of acrylate and methacrylate, or of hydrogel or silicone. Those having ordinary skill in the art will appreciate that in fact any soft biocompatible material that exhibits a requisite index of refraction for a particular application of the lens can be employed for generating a lens of the invention, such as the above exemplary lens 10.

The refractive surface 16 exhibits an undulating topography. For purposes of illustration, the surface modulations have been exaggerated. More specifically, the refractive surface 16 can be characterized by a base curvature or profile 18, depicted by the dashed lines, on which a continuous pattern 20 of surface deviations are superimposed. The exemplary base profile 18 is generally spherical and is radially symmetric about an optical axis 22 of the lens body/optic 12. Similarly, in this exemplary embodiment, the continuous pattern of surface deviations is also radially symmetric about the optical axis 22. Although the base profile 18 in this embodiment is spherical, in other embodiments, aspherical base profiles can be utilized in the practice of the invention.

Embodiments of the amplitude and/or frequency modulated sinusoidal optic design of the present invention can provide a desired enhanced depth-of-focus optic design. Based on a classical sinusoidal technique, two designs are disclosed, based on amplitude modulation and frequency modulation. A first design attenuates the sinusoidal amplitude of an optic from pupil center to optic periphery to concentrate more light energy to a single focal plane. A second design modulates the sinusoidal periodicity of an optic to vary the effective add-power as a function of pupil radius. Embodiments of the present invention combine the two design types to enhance further the through-focus optic performance and generate a desired depth-of-focus profile. Embodiments of the present invention can be implemented as monofocal, accommodative and/or multifocal intraocular lenses.

The numerical computation used to model the embodiments of the present invention wad performed using the Matlab program. A wave optics approach was selected to model the sinusoidal optic structure and the performance evaluation mainly focuses on the through-focus modulation transfer function at 50 (20/40 VA) and 100 lp/mm (20/20 VA).

The classic sinusoidal design was proposed as an alternative way to generate trifocal behavior without adverse photic effects of sharp diffractive steps in an optic, such as an IOL optic. The sinusoidal curve can be described by Equation 1.

$$y = a\cos\left(\frac{2\pi r^2}{b}\right) \qquad (1)$$

where a is a parameter determining the amplitude of the sinusoidal curve and the diffraction efficiency at different foci, and b is a parameter specifying the periodicity and the add power.

Figure 1B:
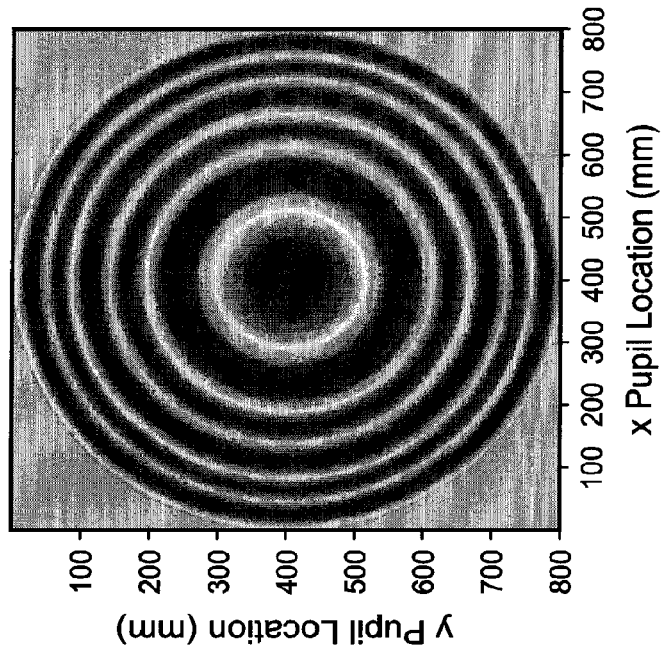
FIGS. 1A and 1B show surface profile plots of a sinusoidal optic design.
Figure 1A:
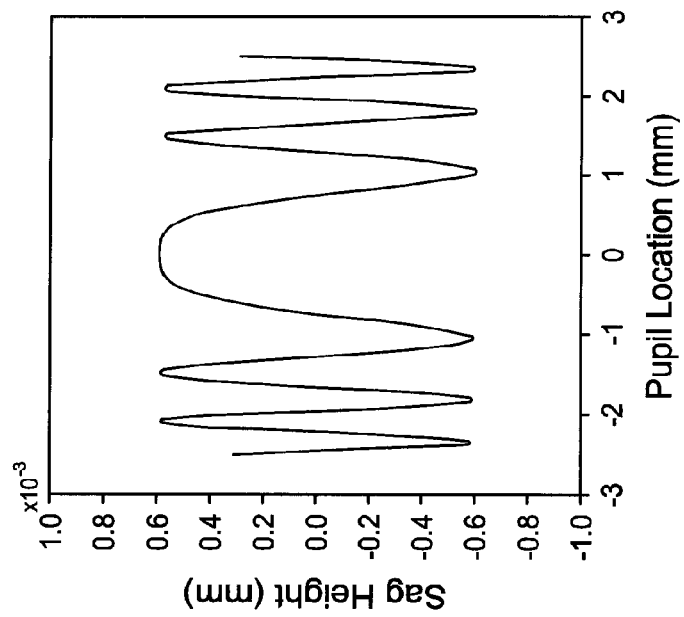
Figure 2C:
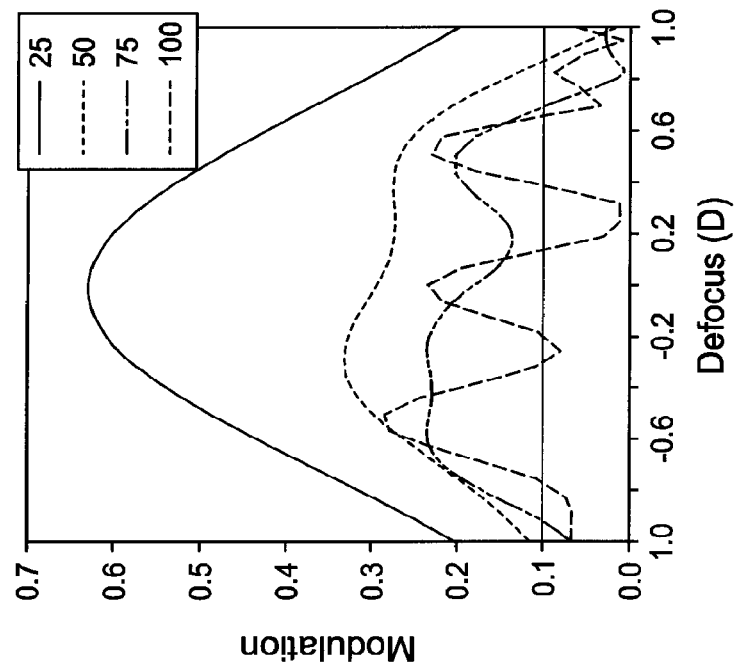
Figure 2D:
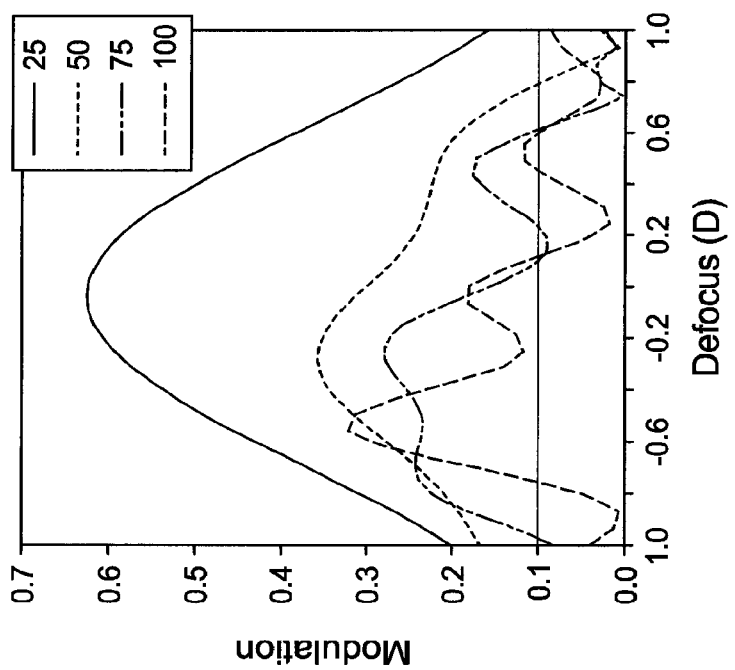

In a study, the parameter values a=0.5877 and b=2.2 were used, which produced ±0.5 D add power. The parameter a can be adjusted to account for the design environment change from air to aqueous humor, as will be discussed herein. An optic surface profile of a sinusoidal optic design is illustrated in FIGS. 1A and 1B. FIG. 1A is a 1-D surface profile plot and FIG. 1B is a surface height map. The sinusoidal curve becomes increasingly dense from the optic/pupil center to the optic periphery, in a manner similar to that of a typical multifocal lens. The through-focus performance of a lens having this design, under the assumption of no high-order aberrations, was computed for a 3.0 mm, 4.5 mm and 5.0 mm pupil inside a conventional wet-cell. FIGS. 2A, 2C and 2D, respectively, illustrate these results.

The computational results reflect faithfully the unique characteristics of a sinusoidal optic design. For small pupils (e.g., about 3 mm), the exposed central portion is dominated by the refractive effect (+0.5 D add) before the interference between periodic structures occurs. The through-focus MTFs peaked at −0.57 D defocus (corresponding to +0.57 D add power), manifesting this effect. The MTF, as shown in FIG. 2B, confirms the good optical quality at this defocus level. At large pupils (4.5 mm and 5.0 mm), the diffractive effects were increasingly obvious, as indicated by three distinctive through-focus peaks at 100 lp/mm. The evaluated wavelength is 550 nm.

Figure 3A:
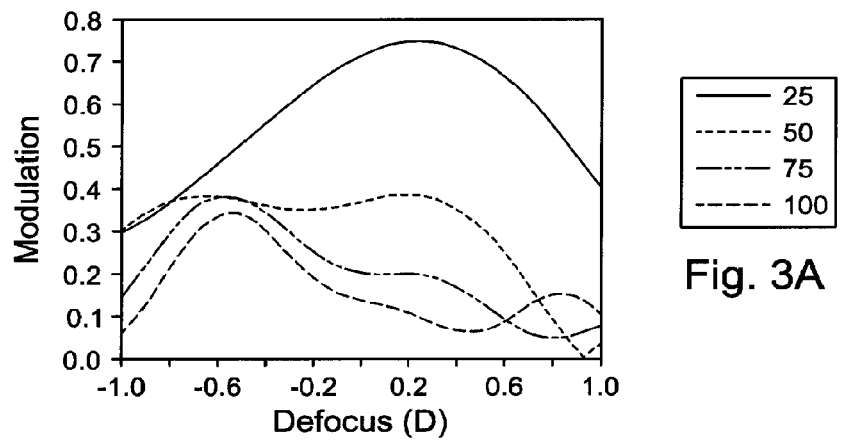
FIGS. 3A-3I illustrate the through-focus performance inside a human eye for a sinusoidal optic design (FIGS. 3A-3C), a spherical lens design (FIGS. 3D-3F), and an aspheric lens design (FIGS. 3G-3I)
Figure 3B:
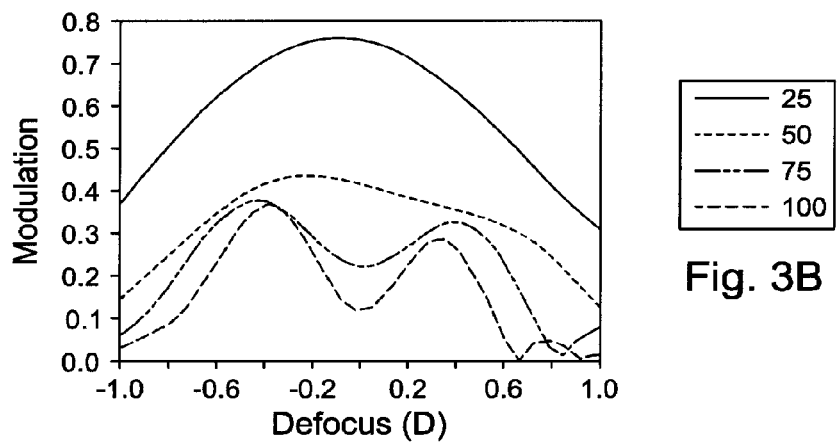
Figure 3C:
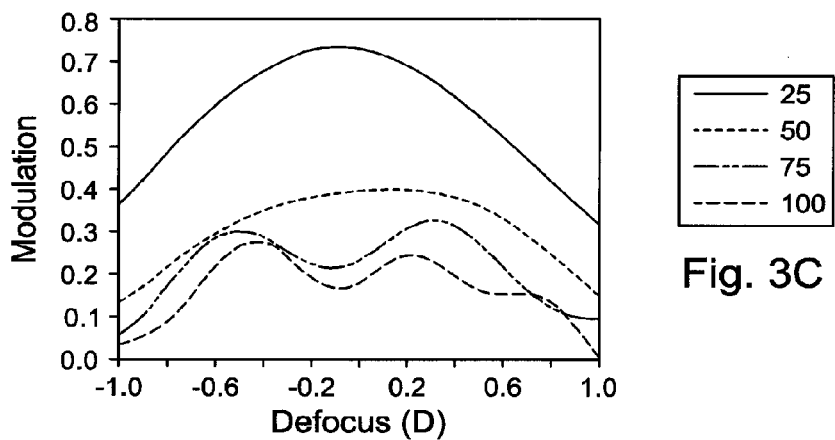
Figure 3D:
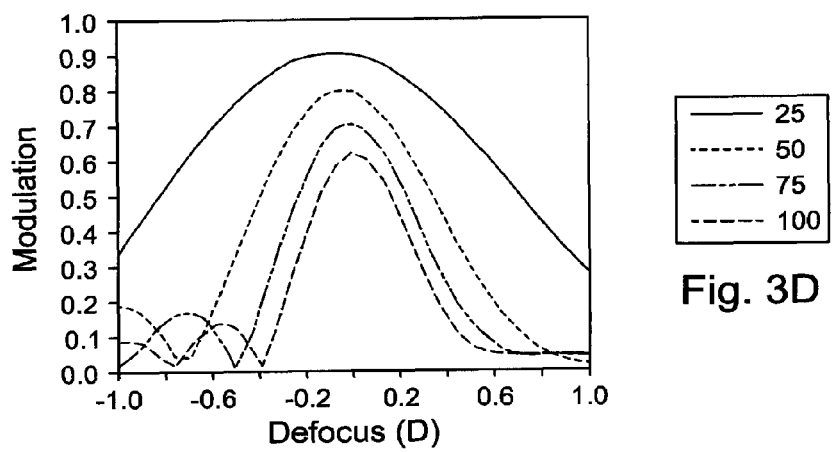
Figure 3E:
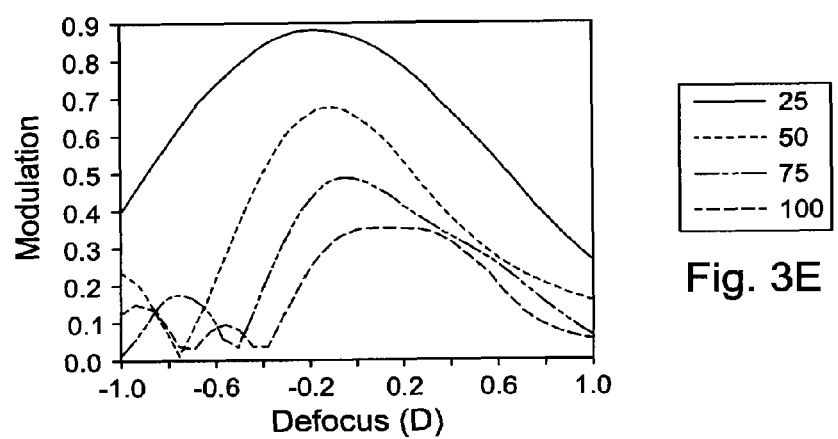
Figure 3F:
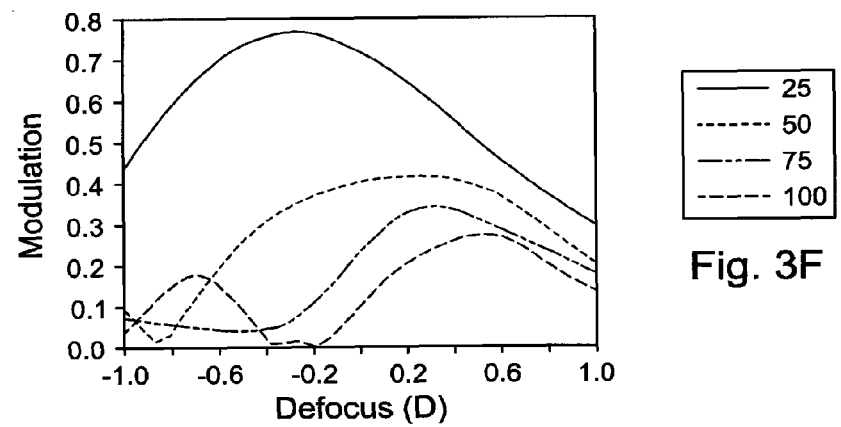
Figure 3G:
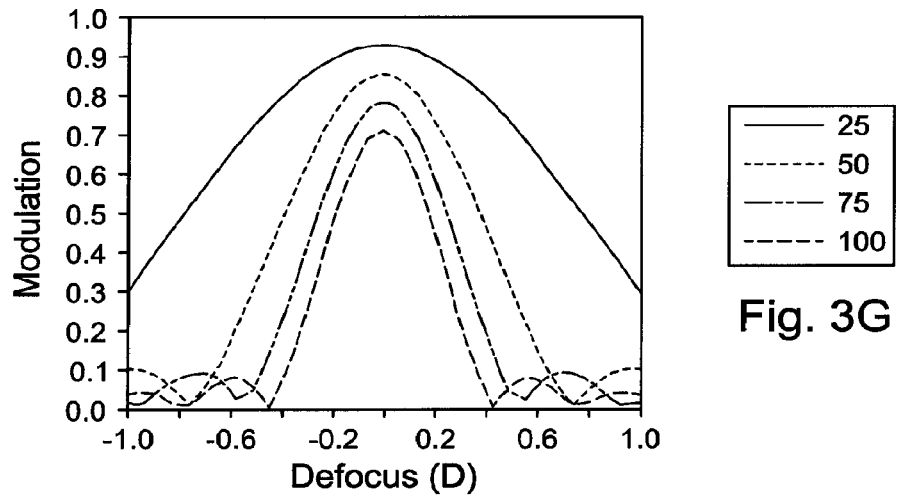
Figure 3H:
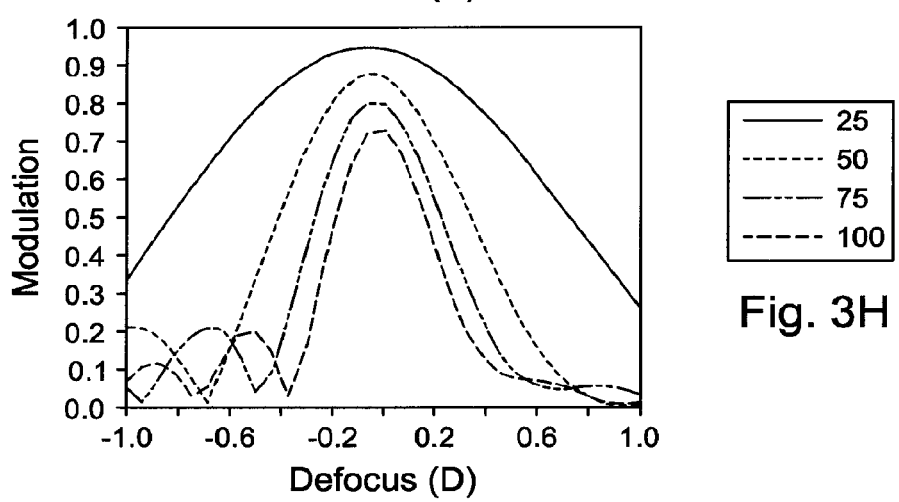
Figure 3I:
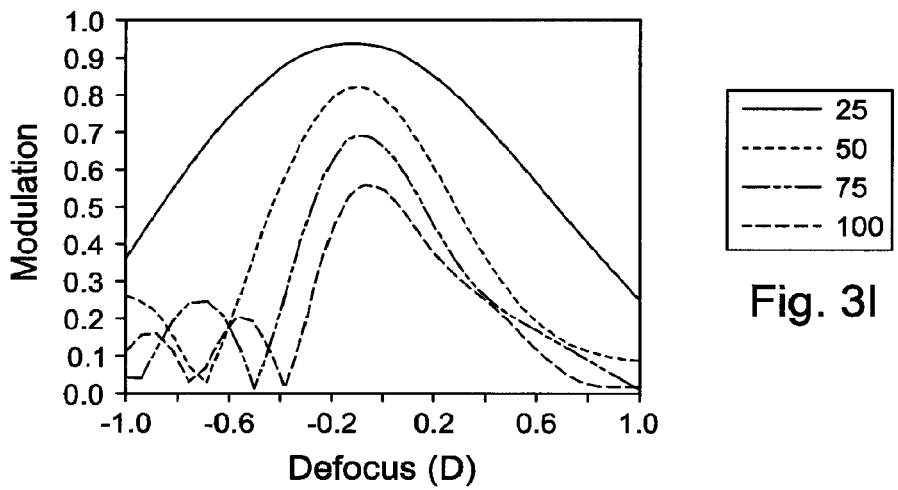

The through-focus performance of the sinusoidal design described above was compared to existing spherical and aspheric IOL optic designs. The results are shown in FIGS. 3A-3I. The through-focus performance inside a human eye (a cornea with 0.28 μm spherical aberration) was computed for the sinusoidal design (FIGS. 3A-3C), a spherical lens design (FIGS. 3D-3F), and an aspheric lens design (FIGS. 3G-3I). The performance at three different pupil sizes was evaluated: 3.5 mm pupil (FIGS. 3A, 3D, 3G); 4.5 mm pupil (FIGS. 3B, 3E, 3H); and 6.0 mm pupil (FIGS. 3C, 3F, 3I). Four typical spatial frequencies were used for evaluation: 25, 50, 75 and 100 lp/mm.

Overall, the sinusoidal design extends the depth-of-focus as compared to the prior art spherical and aspheric IOL optic designs. The large amount of spherical aberration in the spherical optic design reduces the modulation rapidly for large pupils. The aspheric IOL optic design maintains good peak optical performance for all pupils. However, the aspheric lens design has a limited depth-of-focus.

For large pupils, the diffractive effect of the classical sinusoidal design results in the modulation transfer functions being quite low because of light-splitting into three different foci. The reduced modulation transfers typically result in reduced contrast sensitivity and deteriorate night driving performance. In the past, the effect of low modulation transfers in multifocal IOL designs was addressed with an apodization scheme. Similarly, the sinusoidal amplitude of a sinusoidal optic can be modulated with a cosine function which can shift more light to a selected diffraction order, e.g., the 0-diffraction order, as pupil size increases (e.g., in dark conditions).

An amplitude-modulated (AM) sinusoidal optic design is illustrated in FIGS. 4A and 4B. FIG. 4A shows a 1-D surface profile plot and FIG. 4B shows a 2-D surface height map. The cosine modulation function starts from 1.0 at the pupil (optic) center and gradually reduces down to 0 at 5.0 mm pupil diameter. The analytical description of the amplitude modulation is provided by Equation 2.

$$y = a\cos\left(\frac{\pi r}{2r_0}\right)\cos\left(\frac{2\pi r^2}{b}\right) \quad (2)$$

where $r_0$ is the termination pupil radius of the cosine modulation.

Figure 7A:
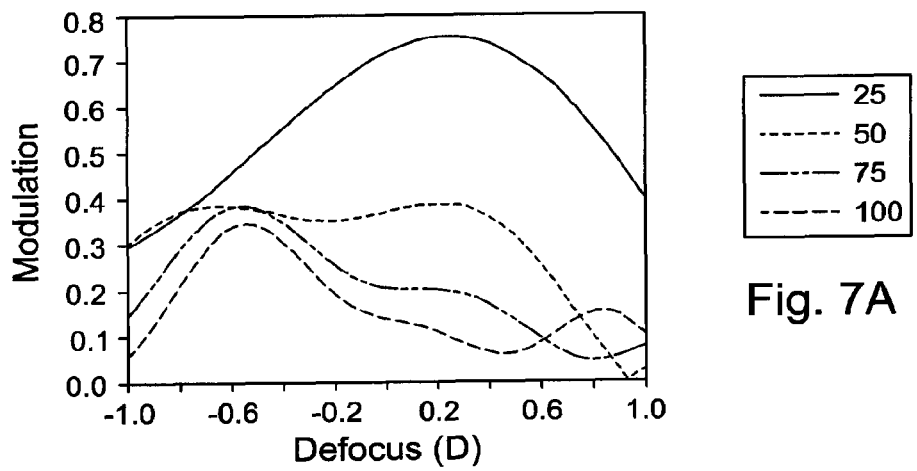
FIGS. 7A-7I illustrate the through-focus performance inside a human eye for a sinusoidal optic design (FIGS. 7A-7C), for an amplitude-modulated sinusoidal optic design (FIGS. 7D-7F) and for an embodiment of the amplitude-modulated and frequency-modulated sinusoidal optic design of the present invention (FIGS. 7G-7I).
Figure 7B:
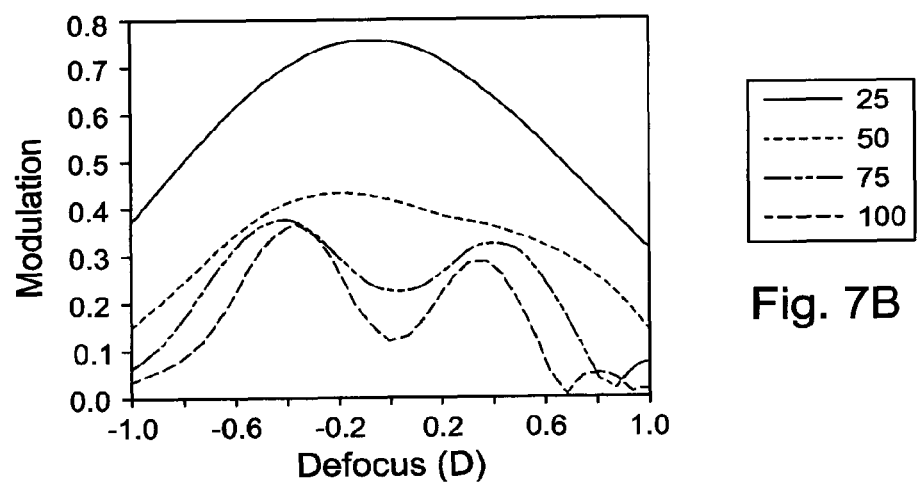
Figure 7C:
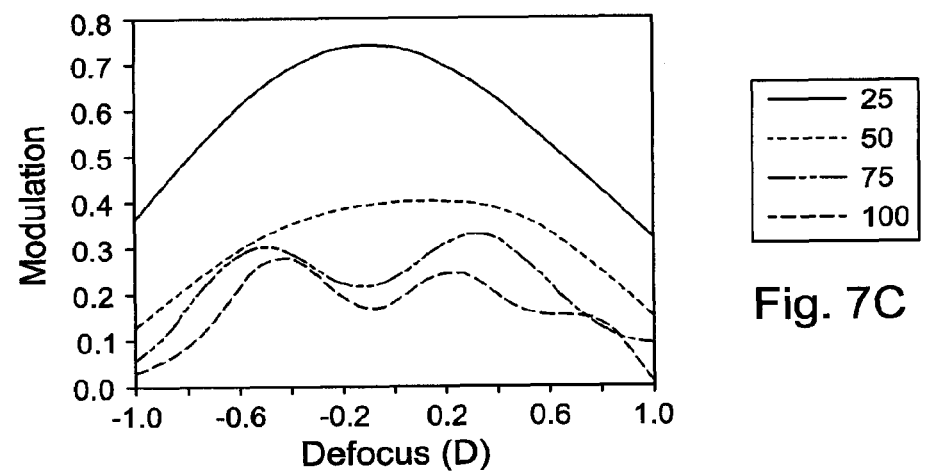
Figure 7D:
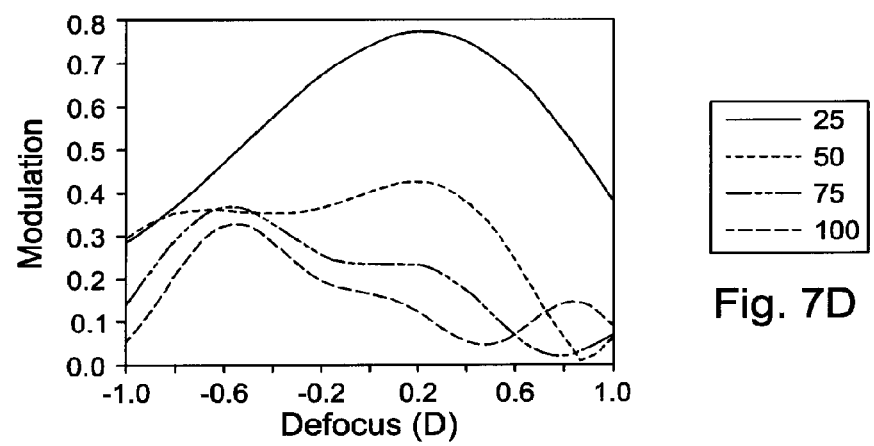
Figure 7E:
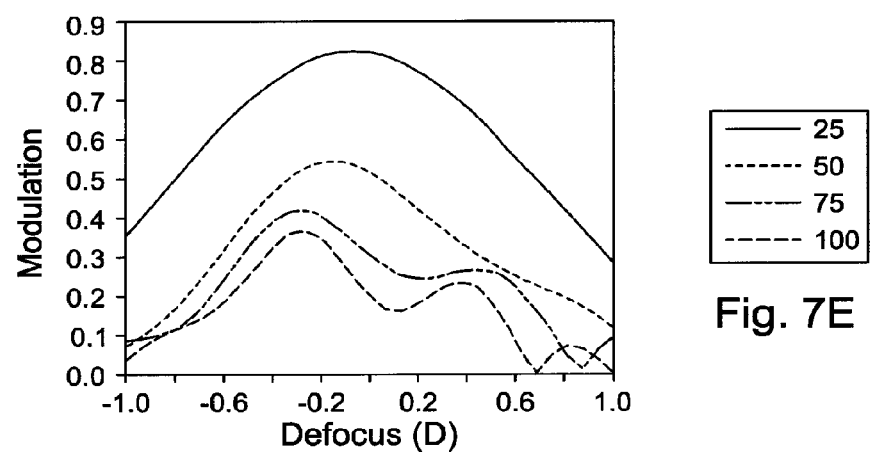
Figure 7F:
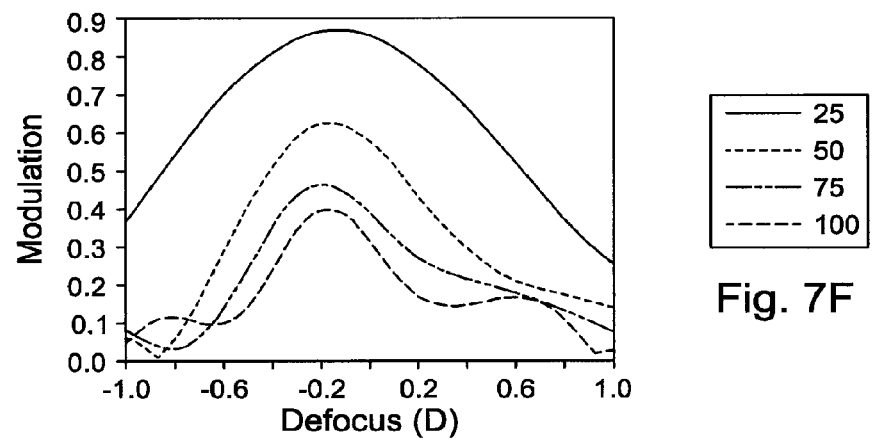

FIGS. 7D-7F illustrate the through-focus performance of the amplitude modulated sinusoidal design, as will be discussed further below. As shown in FIG. 7F, the peak performance of 100 lp/mm for a 6.0 mm entrance pupil has been improved from 0.28 of the sinusoidal design to 0.40 (~40% increase).

An enhanced depth-of-focus may have less benefit for a large pupil (night driving condition) and therefore a reduced depth-of-focus for a large pupil may help to concentrate more energy to a distance focus. A novel technique, frequency-modulation, helped to reduce the add power of the sinusoidal design as pupil size increased. The surface profile of a frequency-modulated sinusoidal optic design is shown in FIGS. 5A and 5B. FIG. 5A shows a 1-D surface profile plot and FIG. 5B shows a 2-D surface height map. FIG. 5A also shows an unmodulated sinusoidal optic design for comparison. Due to the nature of add power reduction, the spacing between peaks becomes sparser from lens/pupil center to lens periphery, which is expressed analytically by Equation 3, below.

$$y = a\cos\left(\frac{2\pi r^2}{bf(r)}\right) \quad (3)$$

where f(r) is the square root of the pupil radius.

To further enhance the optical performance at large pupil size, the embodiments of the present invention combine amplitude modulation and frequency modulation on a sinusoidal optic design, concentrating light energy to a single focal plane. The surface profile of an embodiment of the amplitude and frequency modulated sinusoidal optic design of the present invention can be described by equation (4) and a surface profile is shown in FIGS. 6A and 6B.

$$y = a\cos\left(\frac{\pi r}{2r_0}\right)\cos\left(\frac{2\pi r^2}{bf(r)}\right) \quad (4)$$

Figure 6B:
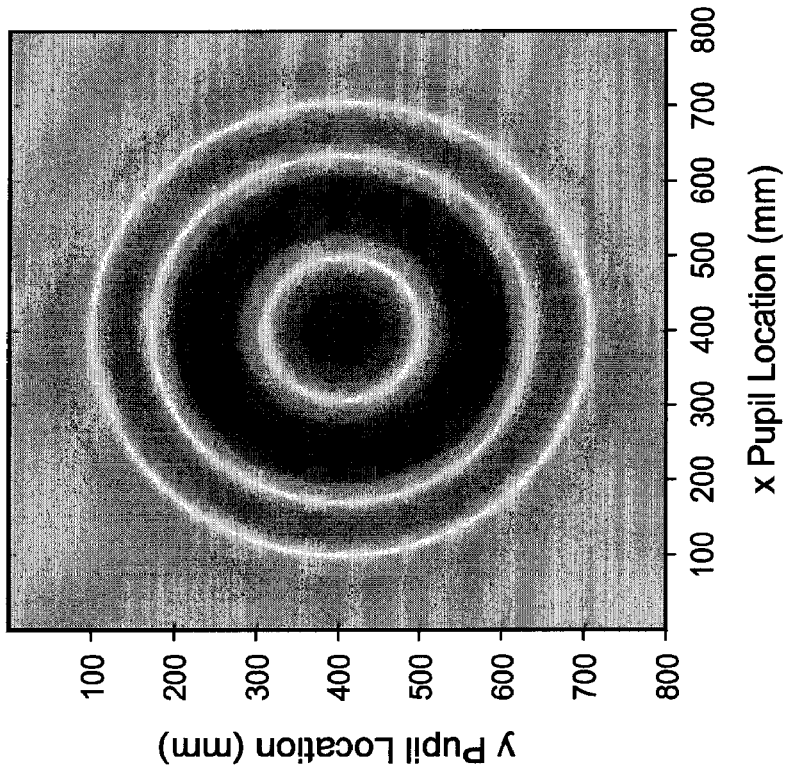
FIGS. 6A and 6B show surface profile plots of an embodiment of the amplitude-modulated and frequency-modulated sinusoidal optic design of the present invention.
Figure 6A:
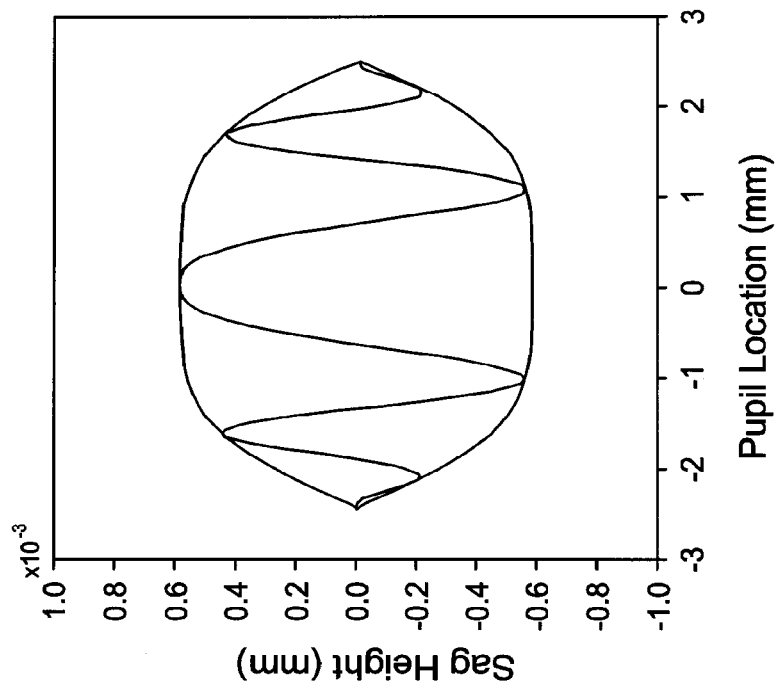

FIG. 6A shows a 1-D surface profile plot and FIG. 6B shows a 2-D surface height map of an embodiment of the amplitude-modulated and frequency-modulated sinusoidal optic design of the present invention. The combination of amplitude-modulation and frequency-modulation improves through-focus performance of an optic significantly. The peak modulation transfers are re-centered to the emmetropic condition for small (3.5 mm) and medium (4.5 mm) pupils, largely due to frequency modulation's effect. The peak MTF performance reached roughly 0.30, 0.40 and 0.50 for 3.5 mm, 4.5 mm and 6.0 mm respectively.

Figure 7G:
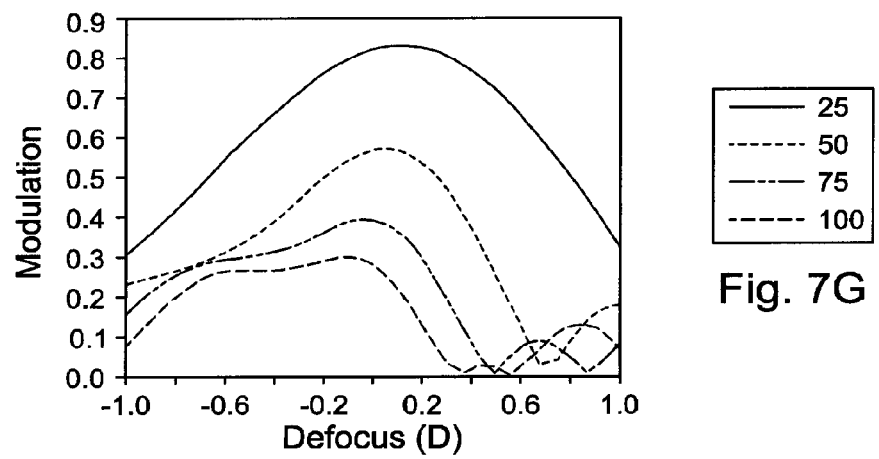
Figure 7H:
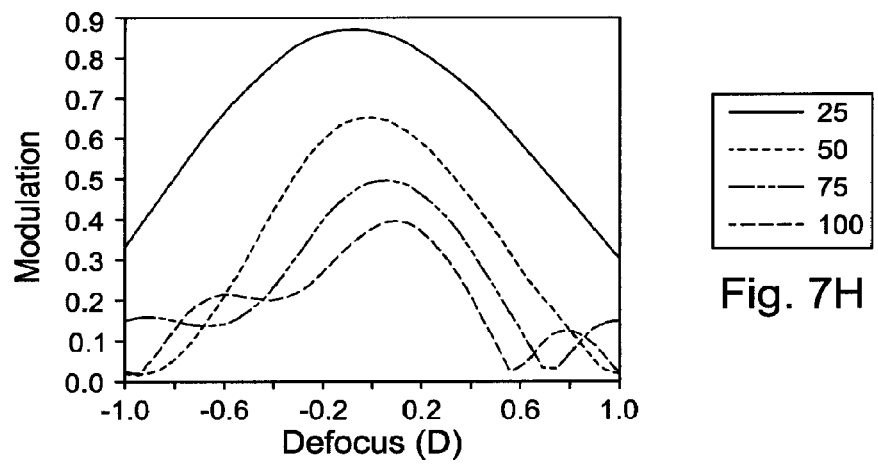
Figure 7I:
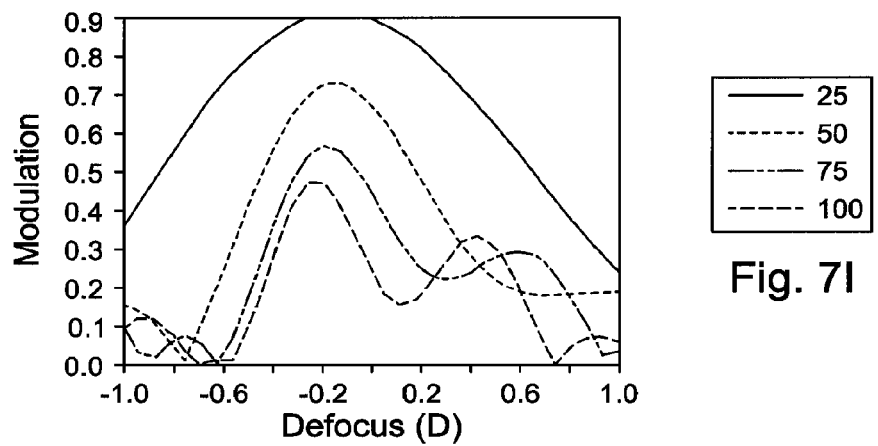

FIGS. 7A-7I illustrate the through-focus performance inside a human eye (a cornea with 0.28 □m spherical aberration) for a sinusoidal optic design (FIGS. 7A-7C), for an amplitude-modulated sinusoidal optic design (FIGS. 7D-7F) and for an embodiment of the amplitude-modulated and frequency-modulated sinusoidal optic design of the present invention (FIGS. 7G-7I). The performance at three different pupil sizes was evaluated: 3.5 mm pupil (FIGS. 7A, 7D, 7G); 4.5 mm pupil (FIGS. 7b, 7E, 7H); and 6.0 mm pupil (FIGS. 7C, 7F, 7I). Four typical spatial frequencies were used for evaluation: 25, 50, 75 and 100 lp/rm.

An ophthalmic lens according to the teachings of the invention can be employed in a variety of vision correction applications. Such applications include, but are not limited to, intraocular lenses (IOLs), contact lenses, intrastromal implants and other refractive devices. For example, a lens of the invention can be employed as an improved IOL that ameliorates residual refractive errors that are typically present after cataract surgery. It is well known in the practice of cataract surgery that factors, such as surgical instrument precision, IOL product precision, preoperative biometry data, surgeon's skill level and capsular bag differences among individuals, can cause variations in a desired refractive error after surgery. One standard deviation of such variations of the refractive error can be as large as 0.5 Diopters. Such residual refractive error, which can persist for a long time, can degrade the patient's visual acuity. Consequently, many patients require spectacles to achieve enhanced post-operative visual acuity.

An IOL formed in accordance with the teachings of the invention can be utilized to render outcomes of cataract surgery more predictable, thus reducing dependence on spectacles after cataract surgery. In particular, an IOL of the invention can include a refractive surface having surface deviations that cause an enhancement of the IOL's depth of field, and hence lower the IOL's sensitivity to errors described above. In other words, an eye of a patient in which an IOL of the invention is implanted exhibits an increased depth of focus, and hence provides improved visual performance within a wider range of defocus. Accordingly, post-operative variations in refractive error have a reduced impact on the patient's visual performance.

Those having ordinary skill in the art will appreciate that various modifications can be made to the above embodiments without departing from the scope of the invention.

The invention claimed is:
1. An ophthalmic lens, comprising:
an optic having an anterior surface and a posterior surface disposed about an optical axis, wherein:
at least one of the surfaces has a profile characterized by superposition of a base profile and an auxiliary profile, the auxiliary profile comprising a continuous pattern of surface deviations from the base profile, wherein the auxiliary profile is a sinusoidal profile, and wherein the sinusoidal profile is amplitude and frequency modulated with a cosine function operable to shift light to a selected focal plane, wherein the amplitude and frequency modulated profile of the surface having said auxiliary profile is defined by the following relation:

$$y = a\cos\left(\frac{\pi r}{2r_0}\right)\cos\left(\frac{2\pi r^2}{bf(r)}\right)$$

wherein,
- y denotes the continuous pattern of surface deviations from the base profile;
- a denotes the amplitude of the sinusoidal curve and the diffraction efficiency at different foci;
- b denotes the periodicity and add power;
- r denotes a radial distance from an optical axis of the lens;
- $r_0$ is the termination pupil radius of the cosine modulation; and
- f(r) is the square root of the pupil radius.

2. The ophthalmic lens of claim 1, wherein the anterior surface and the posterior surface are convex.

3. The ophthalmic lens of claim 1, where in the anterior surface and the posterior surface are concave.

4. The ophthalmic lens of claim 1, wherein the base profile is spherical.

5. The ophthalmic lens of claim 1, wherein the base profile is symmetric about an optical axis of the ophthalmic lens.

6. The ophthalmic lens of claim 1, wherein the base profile is aspherical.

7. The ophthalmic lens of claim 1, wherein the auxiliary profile is symmetric about an optical axis of the ophthalmic lens.

8. The ophthalmic lens of claim 1, wherein the ophthalmic lens comprises an IOL.

9. The ophthalmic lens of claim 8, wherein the IOL is a monofocal IOL.

10. The ophthalmic lens of claim 8, wherein the IOL is an accommodative IOL.

11. The ophthalmic lens of claim 8, wherein the IOL is a multifocal IOL.

12. The ophthalmic lens of claim 1, wherein the anterior surface and the posterior surface are refractive surfaces.

13. An ophthalmic lens, comprising:
an optic having an anterior surface and a posterior surface disposed about an optical axis, wherein:
at least one of the surfaces has a profile characterized by superposition of a base profile and an auxiliary sinusoidal profile, the auxiliary sinusoidal profile comprising a continuous pattern of surface deviations from the base profile, wherein the auxiliary sinusoidal profile is modulated with a cosine function as defined by at least one of the following equations:

$$y = a\cos\left(\frac{\pi r}{2r_0}\right)\cos\left(\frac{2\pi r^2}{b}\right); \text{ and}$$

$$y = a\cos\left(\frac{\pi r}{2r_0}\right)\cos\left(\frac{2\pi r^2}{bf(r)}\right);$$

wherein,
- y denotes the continuous pattern of surface deviations from the base profile;
- a denotes the amplitude of the sinusoidal curve and the diffraction efficiency at different foci;
- b denotes the periodicity and add power;
- r denotes the radial distance from the optical axis of the lens;
- $r_0$ denotes the termination pupil radius of the cosine modulation; and
- f(r) denotes the square root of r.

14. The ophthalmic lens of claim 13, wherein the anterior surface and the posterior surface are convex.

15. The ophthalmic lens of claim 13, where in the anterior surface and the posterior surface are concave.

16. The ophthalmic lens of claim 13, wherein the base profile is spherical.

17. The ophthalmic lens of claim 13, wherein the base profile is symmetric about an optical axis of the ophthalmic lens.

18. The ophthalmic lens of claim 13, wherein the base profile is aspherical.

19. The ophthalmic lens of claim 13, wherein the auxiliary profile is symmetric about an optical axis of the ophthalmic lens.

20. The ophthalmic lens of claim 13, wherein the ophthalmic lens comprises an IOL.

21. The ophthalmic lens of claim 20, wherein the IOL is a monofocal IOL.

22. The ophthalmic lens of claim 20, wherein the IOL is an accommodative IOL.

23. The ophthalmic lens of claim 20, wherein the IOL is a multifocal IOL.

24. The ophthalmic lens of claim 13, wherein the anterior surface and the posterior surface are refractive surfaces.

* * * * *